US008012721B2

(12) United States Patent
Wahnon et al.

(10) Patent No.: US 8,012,721 B2
(45) Date of Patent: *Sep. 6, 2011

(54) METHOD FOR GLUCOSE PRODUCTION USING ENDOGLUCANASE CORE PROTEIN FOR IMPROVED RECOVERY AND REUSE OF ENZYME

(75) Inventors: Daphne Wahnon, Ottawa (CA); Theresa C. White, Ottawa (CA); Jennifer Donaldson, Ottawa (CA); Jeffrey S. Tolan, Ottawa (CA)

(73) Assignee: Iogen Energy Corporation, Ontario (CA)

( * ) Notice: Subject to any disclaimer, the term of this patent is extended or adjusted under 35 U.S.C. 154(b) by 51 days.

This patent is subject to a terminal disclaimer.

(21) Appl. No.: 10/507,618

(22) PCT Filed: Mar. 5, 2003

(86) PCT No.: PCT/CA03/00299

§ 371 (c)(1),
(2), (4) Date: Aug. 17, 2005

(87) PCT Pub. No.: WO03/078644

PCT Pub. Date: Sep. 25, 2003

(65) Prior Publication Data

US 2006/0008885 A1 Jan. 12, 2006

Related U.S. Application Data

(60) Provisional application No. 60/364,020, filed on Mar. 15, 2002.

(51) Int. Cl.
*C12P 19/02* (2006.01)
(52) U.S. Cl. ......... 435/105; 435/161; 435/200; 435/203
(58) Field of Classification Search .................. None
See application file for complete search history.

(56) References Cited

U.S. PATENT DOCUMENTS

| | | | |
|---|---|---|---|
| 3,932,307 A | 1/1976 | Setterquist | |
| 4,237,226 A | 12/1980 | Grethlein | |
| 4,409,329 A * | 10/1983 | Silver | 435/105 |
| 4,461,648 A | 7/1984 | Foody | |
| 4,728,613 A * | 3/1988 | Brewer et al. | 435/222 |
| 4,826,566 A | 5/1989 | Burkart | |
| 4,894,338 A | 1/1990 | Knowles et al. | |
| 5,120,463 A | 6/1992 | Bjork et al. | |
| 5,298,405 A | 3/1994 | Nevalainen et al. | |
| 5,712,142 A | 1/1998 | Adney et al. | |
| 5,730,837 A | 3/1998 | Black et al. | |
| 5,837,515 A | 11/1998 | Suominen et al. | |
| 5,859,236 A | 1/1999 | Burkart | |
| 5,861,271 A | 1/1999 | Fowler et al. | |
| 5,866,407 A * | 2/1999 | Foody et al. | 435/263 |
| 5,874,276 A | 2/1999 | Fowler et al. | |
| 5,922,579 A | 7/1999 | Fagerstrom et al. | |
| 6,090,595 A | 7/2000 | Foody et al. | |
| 6,184,019 B1 | 2/2001 | Miettinen-Oinonen et al. | |
| 6,228,629 B1 | 5/2001 | Paloheimo et al. | |
| 6,562,340 B1 * | 5/2003 | Bedford et al. | 424/94.61 |
| 2004/0053373 A1 * | 3/2004 | Foody et al. | 435/105 |

FOREIGN PATENT DOCUMENTS

| | | |
|---|---|---|
| EP | 0 866 165 A | 9/1998 |
| EP | 0 866 165 | 10/2007 |
| WO | 95/16782 | 6/1995 |

OTHER PUBLICATIONS

Tolan J.S., Clean Techn Environ Policy 3, Feb. 2002, p. 339-345.*
Lawford et la., Applied Biochemistry & Biotechnology, 2001, vol. 91-93, p. 133-146.*
Tolan J.S. , Clean Techn Environ Policy 3, Feb. 2002, p. 339-345.*
Ju et al., Biotechnol. Prog. 1999, vol. 15, p. 91-97.*
Suurnäkki et al., Cellulose, 2000, vol. 7, p. 189-209.*
Tolan, T.S., Clean Techn Environ Policy 3, Feb. 2002, p. 339-345.*
Karlsson et al., Applied Biochemistry and Biotechnology, 1999, vol. 82, p. 243-258.*
McCarter et al., Applied Biochemistry and Biotechnology, 2002, vol. 98-100, p. 273-287.*
Duarte, et al., "Aspergilli and Lignocellulosics: Enzymology and biotechnological applications"; FEMS Microbiology Reviews 13 (1994) 377-86.
Ooshima, et al., "Enhancement of Enzymatic Hydrolysis of Cellulose by Surfactant"; Biotechnology and Bioengineering, vol. XXVIII (1986) 1727-34.
Kaar, et al., "Benefits from Tween During Enzymic Hydrolysis of Corn Stover"; Department of Chemical Engineering, Texas A&M University; Biotechnology and Bioengineering, vol. 59, No. 4 (1998) 419-27.
Eriksson, et al., "Mechanism of Surfactant Effect in Enzymatic Hydrolysis of Lignocellulose"; Enzyme and Microbial Technology vol. 31 (2002) 353-64.
Karlsson, et al., Hydrolysis of Steam-Pretreated Lignocellulose; Applied Biochemistry and Biotechnology; vol. 82, No. 3 (1999) 243-58.
Henrissat, et al., "Synergism of Cellulases from Trichoderma Reesei in the Degradation of Cellulose"; Biotechnology, vol. 3 (1985) 722-26.
Schulein, "Enzymatic Properties of Cellulases from Humicola Insolens"; Journal of Biotechnology vol. 57 (1997) 71-81.
Srisodsuk, "Mode of Action of Trichoderma Reesei Cellbiohydrolase I on Crystalline Cellulose"; VTT Biotechnology and Food Research (1994) 3-109.

(Continued)

*Primary Examiner* — Kade Ariani
(74) *Attorney, Agent, or Firm* — Fitzpatrick, Cella, Harper & Scinto

(57) ABSTRACT

The present invention pertains to a method of converting cellulose to glucose by treating a pretreated lignocellulosic substrate with an enzyme mixture comprising cellulase enzyme and endoglucanase core proteins, wherein the endoglucanase core proteins are present in the enzyme mixture at an amount relative to all endoglucanases from about 35 wt. % to about 100 wt. % and wherein the endoglucanase cellulase enzymes are present in the enzyme mixture at an amount relative to the amount of CBH and EG enzymes from about 2 wt. % to about 50 wt. %. The pretreated lignocellulosic substrate is selected from the group consisting of agricultural residues, residues after starch or sugar removal, dedicated ethanol crops, forestry products, and pulp and paper products, or combinations thereof.

21 Claims, 2 Drawing Sheets

OTHER PUBLICATIONS

Kotiranta, et al., "Adsorption and Activity of *Trichoderma reesei* Cellobiohydrolase I, Endoglucanase II, and the Corresponding Core Proteins on Steam Pretreated Willow"; Applied Biochemistry and Biotechnology, vol. 81, No. 2 (1999) 81-90.

Van Tilbeurgh, et al., "Limited Proteolysis of the Cellobiohydrolase I from *Trichoderma reesei*"; FEBS Letters, vol. 204, No. 2 (1986) 223-27.

Chen, et al., "Three Forms of Cellobiohyrdolase I from *Trichoderma reesei*"; Biochemistry and Molecular Biology International, vol. 30, No. 5 (1993) 901-10.

Tomme, et al., "Studies of the Cellulolytic System of *Trichoderma reesei* QM 9414"; Eur. J. Biochem., vol. 170 (1988) 575-81.

Suumakki, et al., "*Trichoderma reesei* Cellulases and their Core Domains in the Hydriolysis and Modification of Chemical Pulp"; Cellulose, vol. 7 (2000) 189-209.

Nidetzky, et al., "Cellulose Hydrolysis by the Cellulases from *Trichoderma reesei*: A New Mode for Synergistic Interaction"; Biochem. J., vol. 298 (1994) 705-10.

Baker, et al., "Hydrolysis of Cellulose Using Ternary Mixtures of Purified Cellulases"; Applied Biochemistry and Biotechnology, vol. 70-72, (1998) 395-403.

Van Tilbeurgh, et al., "Separation of Endo- and Exo-type Cellulases using a New Affinity Chromatography Method"; vol. 169, No. 2 (1984) 215-18.

Pakula, et al., "Monitoring the Kinetics of Glycoprotein Synthesis and Secretion in the Filamentous Fungus *Trichoderma reesei*: Cellobiohydrolase I (CBHI) as a Model Protein": Microbiology, vol. 146 (2000) 223-32.

Vinzant, et al., "Fingerprinting *Trichoderma reesei* Hydrolases in a Commercial Cellulase Preparation"; Applied Biochemistry and Biotechnology, vol. 91 (2001) 99-107.

Moeti, et al., "Characterization of Phase and Emulsion Behavior . . . ", Clark Atlanta University (2001) 4-5.

Kotiranta, et al., "Adsorption and Activity of *Trichoderma reesei* Cellobiohydrolase I, Endoglucanase II, and the Corresponding Core Proteins on Steam Pretreated Willow", Appl. Biochem. Biotechnol., vol. 81 (1999) 81-90.

Kraulis, et al., "Determination of the Three-Dimensional Solution Structure of the C-Terminal Domain of Cellobiohydrolase I from *Trichoderma reesei*. A Study Using Nuclear Magnetic Resonance and Hybrid Distance Geometry-Dynamical Simulated Annealing", Biochemistry, vol. 28 (1989) 7241-57.

Mattinen, et al., "Three-dimensional structures of three engineered cellulose-binding domains of cellobiohydrolase I from *Trichoderma reesei*", Prot. Sci., vol. 6 (1997) 294-303.

Xu, et al., "Solution Structure of a Cellulose-Binding Domain from Cellulomonas fimi by Nuclear Magnetic Resonance Spectroscopy", Biochemistry, vol. 34 (1995) 6993-7009.

UniProt Entries for the *Acidothermus cellulolyticus* E1 (P54583), 1996.

UniProt Entries for *Trichoderma reesei* EG-II (P07982), 1988.

B.B. Bauminger, "Micro method for manual analysis of true glucose in plasma without deproteinization", J. clin. Path. 1974, 27, 1015-1017.

Neil R. Gilkes, et al. "The Adsorption of a Bacterial Cellulase and Its Two Isolated Domains to Crystalline Cellulose", The Journal of Biological Chemistry, vol. 267, No. 10, Issue of Apr. 5, pp. 6743-6749, 1992.

Pia Kotiranta, et al., "Adsorption and Activity of *Trichoderma reesei* Cellobiohydrolase I, Endoglucanase II, and the Corresponding Core Proteins on Steam Pretreated Willow", Applied Biochemistry and Biotechnology, vol. 81, (1999) pp. 81-90.

Diane Knappert, et al. "Partial Acid Hydrolysis of Cellulosic Materials as a Pretreatment for Enzymatic Hydrolysis", Biotechnology and Bioengineering, vol. XXII, pp. 1449-1463 (1980).

Frank H. Bissett, "Analysis of Cellulase Proteins by High-Performance Liquid Chromatography", Journal of Chromatography, 178 (1979) 515-523.

Ramagauri Bhikhabhai, et al., "Isolation of Cellulolytic Enzymes from *Trichoderma reesei* QM 9414", Journal of Applied Biochemistry, 6, 336-345 (1984).

Hans E. Grethlein, et al. "Common Aspects of Acid Prehydrolysis and Steam Explosion for Pretreating Wood", Bioresource Technology, 36 (2)(1991), 77-82.

Bernard Henrissat, et al., "Structural and sequence-based classification of glycoside hydrolases", Current Opinion in Structural Biology, 1997, 7:637-644.

B. Henrissat, et al. "A scheme for designating enzymes that hydrolase the polysaccharides in the cell walls of plants", FEBS Letters, 425 (1998) 352-354.

Joseph P.M. Hui, et al., "Characterization of cellobiohydrolase I (Cel7A) glycoforms from extracts of *Trichoderma reesei* using capillary isoelectric focusing and electrospray mass spectrometry", Journal of Cromatography B, 752, (2001), 349-368.

Markus Linder, et al. "Identification of functionally important amino acids in the cellulose-binding domain of *Trichoderma reesei* cellobiohydrolase I", Protein Science, 1995, 4:1056-1064.

Markus Linder, et al. "Design of a pH-dependent cellulose-binding domain", FEBS Letters 447 (1999) 13-16.

Ricardo Macarrón, et al. "Family a cellulases: two essential tryptophan residues in endoglucanase III from *Trichoderma reesei*", Biochimica Biophysica Acta, 1245 (1995), 187-190.

Bernd Nidetzky, et al. "Cellulose hydrolysis by the cellulases from *Trichoderma reesei*: adsorptions of two cellobiohydrolases, two endocellulasese and their core proteins on filter paper and their relation to hydrolysis", Biochem J. (1994) 303, 817-823.

Merja Penttilä, et al., "Homology between cellulase genes of *Trichoderma reesei*: complete nucleotide sequence of the endoglucanase I gene", Gene, 45 (1986) 253-263.

M. Saloheimo, et al. "EGIII, a new endoglucanase from *Trichoderma reesei*: the characterization of both gene and enzyme", Gene, 63 (1988) 11-21.

Martin Schulein, et al. "Cellulases and other glycan hydrolases families", Proceedings from CIFAR Conference XIV, UC Davis, Jun. 4, 2001.

S. Shoemaker, et al. "Molecular Cloning of Exo-Cellobiohydrolase I Derived from *Trichoderma reesei* Strain L27", Bio/Technology 1, 691-696 (1983).

Jerry Stalhberg, et al. "A binding-site-deficient, catalytically active, core protein of endoglucanase III from the culture filtrate of *Trichoderma reesei*", Eur. J. Biochem. 173, 179-183 (1988).

Tuula Teeri, et al. "Homologous domains in *Trichoderma reesei* cellulolytic enzymes: gene sequence and expression of cellobiohydrolase II",Gene, 51, 43-52 (1987).

Tuula Teeri, et al., "Domain function in *Trichoderma reesei* cellobiohydrolases", Journal of Biotechnology, 24 (1992) 169-176.

Peter Tomme, et al. "Studies of the cellulolytic system of *Trichoderma reesei* QM 9414",Eur. J. Biochem. 170, 575-581 (1988).

Kotiranta, et al., "Adsorption and Activity of *Trichoderma reesei* Cellobiohydrolase I, Endoglucanase II, and the Corresponding Core Proteins on Steam Pretreated Willow", Appl. Biochem. Biotechnol. vol. 81, No. 2 (1999) 81-90.

Van Tilbeurgh, et al., "Limited proteolysis of the cellobiohydrolase I from *Trichoderma reesei*", FEBS, vol. 204, No. 2 (1986) 223-27.

Chen, et al., "Three Forms of Cellobiohydrolase I from *Trichoderma reesei*", Biochem. Mol. Biol. Intl., vol. 30, No. 5 (1993) 901-10.

Tomme, et al., "Studies of the cellulolytic system of *Trichoderma reesei* QM 9414", Eur. J. Biochem., vol. 170 (1988) 575-81.

Suurnakki, et al., "*Trichoderma reesei* cellulases and their core domains in the hydrolysis and modification of chemical pulp", Cellulose, vol. 7 (2000) 189-209.

Nidetzky, et al., "Cellulose hydrolysis by the cellulases from *Trichoderma reesei*: a new model for synergistic interaction.", Biochem. J., vol. 298 (1994) 705-10.

Baker, et al., "Hydrolysis of Cellulose Using Ternary Mixtures of Purified Cellulases.", Appl. Biochem. Biotechnol., vol. 70-72 (1998) 395-403.

Van Tilbeurgh, et al., "Separation of endo- and exo-type cellulases using a new affinity chromatography method", FEBS, vol. 169, No. 2 (1984) 215-18.

Pakula, et al., "Monitoring the kinetics of glycoprotein synthesis and secretion in the filamentous fungus *Trichoderma reesei*: cellobiohydrolase I (CBHI) as a model protein", Microbiology, vol. 146 (2000) 223-32.

Vinzant, et al., "Fingerprinting *Trichoderma reesei* Hydrolases in a Commercial Cellulase Preparation", Appl. Biochem. Biotechnol., vol. 91-93 (2001) 99-107.

Sigma Aldrich Catalogue for Novozym 188 Enzyme Preparation 2008.

Duarte, et al., "Aspergilli and lignocellulosics: Enzymology and biotechnological applications", FEMS Microbiol. Rev., vol. 13 (1994) 377-86.

Ooshima, et al., "Enhancement of Enzymatic Hydrolysis of Cellulose by Surfactant", Biotechol, Bioeng., vol. 28 (1986) 1727-34.

Kaar, et al., "Benefits from Tween During Enzymic Hydrolysis of Corn Stover", Biotechnol. Bioeng., vol. 59, No. 4 (1998) 419-27.

Eriksson, et al., "Mechanism of surfactant effect in enzymatic hydrolysis of lignocellulose", Enzyme Microbial Tech., vol. 31 (2002) 353-64.

Henrissat, et al., "Synergism of Cellulase from *Trichoderma reesei* in the Degradation of Cellulose", Biotechnology, vol. 3 (1985) 722-26.

Karlsson, et al., "Hydrolysis of Steam-Pretreated-Lignocellulose", Appl. Biochem. Biotechnol., vol. 82 (1999) 243-58.

Schulein, "Enzymatic properties of cellulases from Humicola insolens", J. Biotechnol, vol. 57 (1997) 71-81.

Srisodsuk, "Mode of action of *Trichoderma reesei* cellbiohydrolase I on crystalline cellulose", Academic Dissertation, VTT Publications, vol. 188 (1994) 3-109.

Moeti, et al., "Characterization of Phase and Emulsion Behavior, Surfactant Retention, and Oil Recovery for Novel Alcohol Ethoxycarboxylate Surfactants", US Department of Energy Final Technical Report (2001) 4-5.

Barr et al., "Identification of Two Functionally Different Classes of Exocellulases", Biochemistry, vol. 35 (1996) 586-592.

Beldman et al., "Adsorption and Kinetic Behavior of Purified Endoglucanases and Exoglucanases from *Tricohderma viride*", Biotechnology and Bioengineering, vol. XXX (1987) 251-57.

Birch, "Targeted differential display of abundantly expressed sequences from the basidiomycete Phanerochaete chrysosporium which contain regions coding for fungal cellulose-binding domains", Curr. Genet., vol. 33 (1998) 70-6.

Fan et al., "Evaluation of Pretreatment for Enzymatic Conversation of Agricultural Residues", Biotechnology and Bioengineering Symp., vol. 11 (1981) 29-45.

Foody et al., "Final Report. Optimization of Steam Explosion Pretreatment", U.S. Department of Energy Report ET230501, U.S. Department of Energy, Section 9 and Appendix C (1980) 201-33 and 313-29.

Grohmann et al., "Optimization of Dilute Acid Pretreatment of Biomass", Biotechnology and Bioengineering Symp., vol. 15 (1985) 59-80.

Henrissat, "Enzymology of Cell-Wall Degradation", Biochem. Soc. Trans., vol. 26 (1998) 153-56.

Henrissat et al., "Updating the sequence-based classification of glycosyl hydrolases", Biochemical Journal, vol. 316 (1996) 695-96.

Kim et al., "Adsorption behaviors of two cellobiohydrolases and their core proteins from *Trichoderma reesei* on Avicel PH 101", Biotechnology Letters, vol. 19, No. 9 (1997) 893-97.

Knappert et al., "Partial Acid Hydrolysis of Cellulosic Materials as a Pretreatment for Enzymatic Hydrolysis", Biotechnology and Bioengineering, vol. XXII (1980) 1449-63.

Kyriacou et al., "Reversibility and Competition in the Adsorption of *Trichoderma reesei* Cellulase Components", Biotechnol. Bioeng., vol. 33 (1989) 631-37.

Limam et al., "Two cellobiohydrolases of Penicillium occitanis mutant Pol 6: Purification and properties", Enzyme Microb. Technol., vol. 17 (1995) 340-46.

Parsiegla et al., "Crystal Structures of the Cellulase Cel48F in Complex with Inhibitors and Substrates Give Insights into its Processive Action", Biochemistry, vol. 39 (2000) 11238-46.

Saloheimo et al., "Small endoglucanase from *Trichoderma reesei*, cloned by expression in yeast", in Proc. of the Second TRICEL Symp. on *Trichoderma reesei* Cellulases and Other Hydrolases, Found. for Biotech. and Ind. Ferm. Res., Helsinki, Finland, 1993.

Schulein, "Cellulases of *Trichoderma reesei*", Meth. Enzymol., vol. 160 (1988) 234-42.

Shen et al., "Cellobihoydrolase B, a second exo-cellobiohydrolase from the cellulolytic bacterium Cellulomonas fimi", Biochem. J., vol. 311 (1995) 67-74.

Teeri et al., "The Molecular Cloning of the Major Cellulase Gene From *Trichoderma reesei*", Biotechnology, vol. 1 (1983) 696-99.

Teeri et al., "*Trichoderma reesei* cellobiohydrolases: why so efficient on crystalline cellulose?", Biochem Soc. Trans., vol. 26 (1998) 173-78.

Teeri et al., "Cellulose degradation by native and engineered fungal cellulases" Carbohydr. Eur., vol. 12 (1995) 28-33.

Baker et al., "Hydrolysis of Cellulose Using Ternary Mixtures of Purified Cellulases", Appl. Biochem. Biotechnol., vol. 70-72 (1998) 395-403.

Baker et al., "Synergism Between Purified Bacterial and Fungal Cellulases", In Enzymatic Degradation of Insoluble Carbohydrates, ACS Series 618 (1995) 113-41.

Belaich et al., "Cel9M, a New Family 9 Cellulase of the Clostridium cellulolyticum Cellulosome", J. Bacteriol., vol. 184, No. 5 (2002) 1378-84.

Collen et al., "Extraction of endoglucanase I (Cel7B) fusion proteins from Trichoderma reesei culture filtrate in a poly (ethylene glycol)— phosphate aqueous two-phase system", J. Chromatography A, vol. 943 (2001) 55-62.

Foreman et al., "Transcriptional Regulation of Biomass-degrading Enzymes in the Filamentous Fungus Trichoderma reesei", J. Biol. Chem., vol. 278, No. 34 (2003) 31988-997.

Gal et al., "CelG from Clostridium cellulolyticum: a Multidomain Endoglucanase Acting Efficiently on Crystalline Cellulose", J. Bacteriol., vol. 179, No. 21 (1997) 6595-601.

Kotiranta et al., "Adsorption and Activity of Trichoderma reesei Cellobiohydrolase I, Endoglucanase II, and the Corresponding Core Proteins on Steam Pretreated Willow", Applied Biochem. Biotech., vol. 81 (1999) 81-90.

Kubicek-Pranz et al., "Characterization of Commercial Trichoderma reesei Cellulase Preparation by Denaturing Electrophoresis (SDS-PAGE) and Immunostaining using Monoclonal Antibodies", Biotechnol. Appl. Biochem., vol. 14 (1991) 317-23.

Medve et al., "Hydrolysis of Microcrystalline Cellulose by Cellobiohydrolase I and Endoglucanase II from Trichoderma reesei: Adsorption, Sugar Production Pattern, and Synergism of the Enzymes", Biotechnol. Bioeng., vol. 59, No. 5 (1998) 621-34.

Nidetzky et al., "Cellulose hydrolysis by the cellulases from Trichoderma reesei: adsorptions of two cellobiohydrolases, two endoglucanases, and their core proteins on filter paper and their relation to hydrolysis", Biochem. J., vol. 303 (1994) 817-23.

Stahlberg, et al., "A binding-site-deficient, catalytically active, core protein of endoglucanase III from the culture filtrate of Trichoderma reesei", Eur. J. Biochm., vol. 173 (1988) 179-83.

Suurnäkki et al., "Trichoderma reesei cellulases and their core domains in the hydrolysis and modification of chemical pulp", Cellulose, vol. 7 (2000) 189-209.

Tolan, "Iogen's process for producing ethanol from cellulosic biomass", Clean Techn. Environ. Policy, vol. 3 (2002) 339-45.

Results from the search of Swiss-Prot Protein Database (2011) 40-69.

* cited by examiner

METHOD FOR GLUCOSE PRODUCTION USING ENDOGLUCANASE CORE PROTEIN FOR IMPROVED RECOVERY AND REUSE OF ENZYME

This is a National Stage entry of PCT Application No. CA/03/00299 filed Mar. 5, 2003, which claims priority from U.S. Provisional Application 60/364,020 filed Mar. 15, 2002, the disclosure of which is incorporated herein by reference.

The present invention relates to the enzymatic conversion of cellulose to glucose. More specifically, the present invention provides a method for the conversion of pretreated lignocellulosic substrates using endoglucanase core proteins, and the recovery and reuse of the endoglucanase core proteins.

BACKGROUND OF THE INVENTION

Cellulose is one of the most abundant polymers found in nature and consists of glucose units connected by beta 1,4 linkages. The beta 1,4 linkages which connect individual glucose units are not easily degraded or depolymerized. However, there exists a variety of cellulase enzymes which are capable of enzymatically hydrolysing cellulose.

Cellulases are enzymes produced by a number of microorganisms which catalyse the hydrolysis of cellulose to products such as glucose, cellobiose, and other cellooligosaccharides. Cellulase is usually a generic term denoting a multienzyme mixture comprising exo-cellobiohydrolases (CBHs), endoglucanases (EGs) and β-glucosidases. Cellulase produced by the filamentous fungi *Trichoderma longibrachiatum* comprises at least two cellobiohydrolase enzymes termed CBHI and CBHII and at least 4 EG enzymes.

Cellulase enzymes work synergistically to hydrolzye cellulose to glucose. CBHI and CBHII generally act on the ends of the glucose polymers in cellulose microfibrils liberating cellobiose (Teeri and Koivula, 1995) while the endoglucanases act at random locations on the cellulose. Together these enzymes hydrolyse cellulose to smaller cello-oligosaccharides such as cellobiose. Cellobiose is hydrolysed to glucose by β-glucosidase. Both the exo-cellobiohydrolases and the endoglucanases are glycosyl hydrolases which hydrolyse the glycosidic bond between two or more carbohydrates or between a carbohydrate and a non carbohydrate moiety.

The genes encoding CBHI, CBH II (Shoemaker et al., 1983; Teeri et al., 1987). EG I and EG II (Penttila et al., 1986; Saloheimo et al., 1988) have been cloned and isolated from filamentous fungi such as *T. reesei* and *T. longibrachiatum*. CBHI, CBH II and most EG proteins consist of a catalytic core domain and a cellulose binding domain (CBD) separated by a flexible linker region. The cellulose binding domain (CBD) promotes adsorption of the enzyme to regions of the cellulosic substrate (Tomme et al., 1988; Gilkes et al, 1992), while the core domain is responsible for catalysing the cleavage of cellulose. The linker region may ensure an optimal interdomain distance between the core domain and the cellulose binding domain (Teeri et al., 1992).

The major endoglucanases EG1, EG2 and EG3 are found at amounts of about 8 to 21% in *Trichoderma* relative to the total cellulase mixture consisting of CBH1, CBH2, EG1, EG2 and EG3 (Bisset, 1979; Hui et al., 2001). Hui et al., have determined EG1, EG2 and EG3 to be present in *Trichoderma* from 8 to 18% relative to the total cellulase mixture with EG3 present from 0 to 6% relative to the total cellulase mixture. Since *Trichoderma* EG3 lacks a cellulose binding domain (DNA sequence disclosed in U.S. Pat. No. 5,475,101), the natural abundance of endoglucanase core protein relative to the total endoglucanase mixture in *Trichoderma* is at most 33 wt % in the enzyme mixture. In *Humicola insolens*, the amount of endoglucanase protein relative to the total cellulase mixture is greater than 50% (Schulein et al.).

Several studies indicate that endoglucanase holo proteins are superior to endoglucanase core proteins for cellulose hydrolysis. EG2core protein from *Trichoderma reesei* does not bind as tightly to cellulose as EG2 (Macarron et. al., 1995; Nidetzky et. al., 1994) The EG2core protein is fully active against small soluble substrates such as the chromophoric glycosides derived from the cellodextrins and lactose. However, its activity against an insoluble cellulosic substrates such as Avicel (a crystalline type of cellulose) is greatly reduced compared to EG2 (Stahlberg et al., 1988; Nidetzcy et. al., 1994). Stahlberg showed that EG2 had seven fold more activity than EG2core. This was attributed to the fact that 79% of the EG2 adsorbed to the cellulose versus only 13% of the EG2core protein. Nidetzly examined the absorption and activities of EG2 and EG2core on filter paper. They disclose that on filter paper EG2 has four times more available sites than EG2core. Activity was found to depend on the extent of binding to the substrate. Kotiranta observed similar binding of EG2 and EG2core on steam pretreated willow, a lignocellulosic substrate. However the extent of cellulose conversion using EG2 or EG2core alone was extremely poor; using EG2core alone the extent of cellulose conversion was 1/2 that observed using EG2 (Kotiranta et al., 1999).

Schulein et al. disclose that by combining a *Humicola Insolens* exo-cellobiohydrolase CBHI and *Humicola Insolens* endoglucanasev in a molar ratio 90:5, a 55% conversion could be achieved in thirty hours. Substitution of endoglucanaseV core for endoglucanase V resulted in an almost 60% decrease in the rate of hydrolysis and the same conversion could only be achieved in 48 hrs.

The conversion of cellulose from cellulosic material into glucose is important in many industrial processes, such as the bioconversion of cellulose to fuel ethanol. Unfortunately, cellulose contained in most plant matter is not readily convertible to glucose, and this step represents a major hurdle in the commercialization of such a process. The efficient conversion of cellulose from cellulosic material into glucose was originally thought to involve liberating cellulose and hemicellulose from their complex with lignin. However, more recent processes focus on increasing the accessibility to cellulose within the lignocellulosic biomass followed by depolymerization of cellulose carbohydrate polymers to glucose. Increasing the accessibility to cellulose is most often accomplished by pretreating the cellulosic substrate.

The goal of most pretreatment methods is to deliver a sufficient combination of mechanical and chemical action so as to disrupt the fiber structure and improve the accessibility of the feedstock to cellulase enzymes. Mechanical action typically includes the use of pressure, grinding, milling, agitation, shredding, compression/expansion, or other types of mechanical action. Chemical action typically includes the use of heat (often steam), acid, and solvents. For example, one of the leading approaches to pretreatment is by steam explosion, using the process conditions described in U.S. Pat. No. 4,461,648 and also in Foody et al., 1980, both of which are incorporated herein by reference In this process, lignocellulosic biomass is loaded into a steam gun and up to 5% acid is optionally added to the biomass in the steam gun or in a presoak prior to loading the steam gun. The steam gun is then filled very quickly with steam and held at high pressure for a set length of cooking time. Once the cooking time elapses, the vessel is depressurized rapidly to expel the pretreated biomass.

Another approach described in U.S. Pat. No. 4,237,226, discloses the pretreatment of oak, newsprint, poplar, and corn stover by a continuous plug-flow reactor, a device that is similar to an extruder. Rotating screws convey a feedstock slurry through a small orifice, where mechanical and chemical action break down the fibers.

Pretreatment has been suggested to enhance delignification of the cellulosic substrate (Fan et al., 1981), create micropores by removing hemicellulose, change the crystallinity of the substrate, reduce the degree of polymerization of the cellulose (Knappert et al., 1980) and increase the surface area of the cellulosic substrate (Grethlein and Converse, 1991; Grohman et al., 1985).

Unfortunately, to date the approach of a pretreatment coupled with enzyme hydrolysis has not been able to produce glucose at a sufficiently low cost and make the conversion of cellulose to ethanol commercially attractive. Even with the most efficient of the current pretreatment processes, the amount of cellulase enzyme required to convert cellulose to glucose is high and this represents a significant cost in ethanol production. The option of adding less cellulase to the system usually decreases the amount of glucose produced to an unacceptable extent. The approach of decreasing the amount of enzyme required by increasing the length of time that the enzyme acts on the cellulose leads to uneconomical process productivity, stemming from the high cost associated with retailing the enzymatic mixtures in hydrolysis tanks.

Thus there is a need within the art to identify new methods that enhance the conversion of cellulose within a cellulosic substrate to glucose. Further there is a need in the art to identify enzymes or mixtures of enzymes which enhance the conversion of cellulose to glucose and which are recoverable, recyclable, and reusable.

It is an object of the present invention to overcome drawback of the prior art.

The above object is met by a combination of the features of the main claims. The sub claims disclose further advantageous embodiments of the invention.

SUMMARY OF THE INVENTION

The present invention relates to the enzymatic conversion of cellulose to glucose.

This invention also pertains to a method of converting cellulose within a cellulosic substrate into glucose comprising; treating a pretreated lignocellulosic substrate with an enzyme mixture comprising cellobiohydrolase, β-glucosidase, and EG enzymes, wherein the EG enzymes comprise from 2 wt % to 50 wt % of the amount of the CBH and EG enzyme present and wherein the endoglucanase core protein (ECP) is present from 35 wt % to 100 wt % of all EGs. Preferably, the amount of the ECP in the cellulase mixture is from about 50 wt % to 90 wt % of all EGs. More preferably, the amount of ECP in the cellulase mixture is from about 60 wt % to about 80 wt % of the EG type enzyme. The enzyme mixture preferably comprises CBH, EG, β-glucosidase, and endoglucanase core proteins. More preferably, the enzyme mixture comprises CBH1, CBH2, EGI, EGII, EGIII, β-glucosidase, and endoglucanase core proteins.

Furthermore, this invention pertains to the above method wherein the ECP is recovered following the step of treating.

This invention also pertains to the method as just described wherein the endoglucanase core protein is selected from EG core, EG core plus linker and EG with inactivated cellulose binding domain.

The present invention embraces methods as defined above wherein the pretreated lignocellulosic substrate is selected from the group consisting of agricultural residues, residues after starch or sugar removal, dedicated ethanol crops, forestry products, and pulp and paper products or combinations thereof. Preferably, the agricultural residues are selected from the group consisting of corn stover, wheat straw, barley straw; soybean stover; the residues after starch or sugar removal are selected from the group consisting of oat hulls, rice hulls, sugar cane bagasse, and corn fibre; the dedicated ethanol crops are selected from the group consisting of switch grass, miscanthus, cord grass, and rye grass; the forestry products are selected from the group consisting of hardwood, softwood, Eucalyptus, and sawdust; and the pulp and paper products is solka floc.

Also included within the present invention, is a method as defined above wherein the pretreated lignocellulosic substrate is present in the enzyme mixture at a concentration of about 1 wt % to about 25 wt % in aqueous slurry. Preferably, the lignocellulosic substrate is present in the enzyme mixture at a concentration of about 10 wt % to about 16 wt % in aqueous slurry.

This invention also provides a method of converting cellulose within a cellulosic substrate into glucose comprising; treating a pretreated lignocellulosic substrate with an enzyme mixture comprising CBH, β-glucosidase, and EG enzyme, wherein the EG enzymes comprise from 2 wt % to 50 wt % of the amount of CBH and EG enzyme present in the mixture, and wherein the endoglucanase core protein is present from 35 wt % to 100 wt % of all EGs. Preferably the enzyme mixture comprises CBHI, CBHI, EG I, EG II, EGIII, β-glucosidase and endoglucanase core protein. Furthermore, it is preferred that the amount of the endoglucanase core protein in the cellulase mixture is from about 50 wt % to 90 wt % of all EGs. More preferably, the amount of endoglucanase core protein in the cellulase mixture is from about 60 wt % to about 80 wt % of all EGs.

Furthermore, this invention pertains to either of the above method wherein the endoglucanase core protein is recovered following the step of treating.

This invention also pertains to the method as just described wherein the endoglucanase core protein is selected from EG core, EG core plus linker and EG with inactivated cellulose binding domain.

The present invention also embraces a method for converting cellulose to glucose comprising treating a pretreated lignocellulosic substrate with an enzyme mixture comprising CBH, β-glucosidase, and endoglucanase core plus linker wherein EG type enzymes within the enzyme mixture comprise from 2 wt % to 50 wt % of the amount of CBH and EG enzyme present and wherein the endoglucanase core plus linker is present from 35 wt % to 100 wt % of all EGs. Preferably, the cellulase enzyme comprises CBH, CBHI, EG I, EG II, EGIII, β-glucosidase. Furthermore, it is preferred that the amount of the endoglucanase core plus linker in the cellulase mixture is from about 50 wt % to 90 wt % of all EGs. More preferably, the amount of endoglucanase core plus linker in the cellulase mixture is from about 60 wt % to about 80 wt % of all EGs. Furthermore, this invention pertains to the above method wherein the endoglucanase core plus linker is recovered following the step of treating.

The present invention also provides a cellulase composition with an enzyme mixture comprising CBHI, CBHI, EG I, EG II, EGIII, β-glucosidase and endoglucanase with an inactivated cellulose binding domain wherein the EG enzymes comprise from 2 wt % to 50 wt % of the CBH and EG enzymes present and wherein the endoglucanase with an inactivated cellulose binding domain is present from 35 wt % to 100 wt % of all EGs. Preferably, the amount of the endoglucanase with an inactivated cellulose binding domain is present in the cellulase mixture is from about 50 wt % to 90 wt % of all EGs. More preferably, the amount of endoglucanase with an inactivated cellulose binding domain is present in the cellulase mixture is from about 60 wt % to about 80 wt % of all EGs. Furthermore, this invention pertains to the above method wherein the endoglucanase with an inactivated cellulose binding domain is recovered following the step of treating.

This summary does not necessarily describe all necessary features of the invention but that the invention may also reside in a sub-combination of the described features.

BRIEF DESCRIPTION OF THE DRAWINGS

These and other features of the invention will become more apparent from the following description in which reference is made to the appended drawings wherein:

FIG. 2 shows a graphical representation of the amount of EG2, EG2:EG2core (50:50) and EG2core remaining in solution after hydrolysis.

FIG. 3 shows a graphical representation of the solution stability of EG2 and EG2core in pH 4.8 citrate buffer and 50 C. Stability is assessed by monitoring the % residual CMC activity of the enzymes. EG2 and EG2 core are found to be equally stable for 15 to 20 days.

DESCRIPTION OF PREFERRED EMBODIMENT

Figure 1:
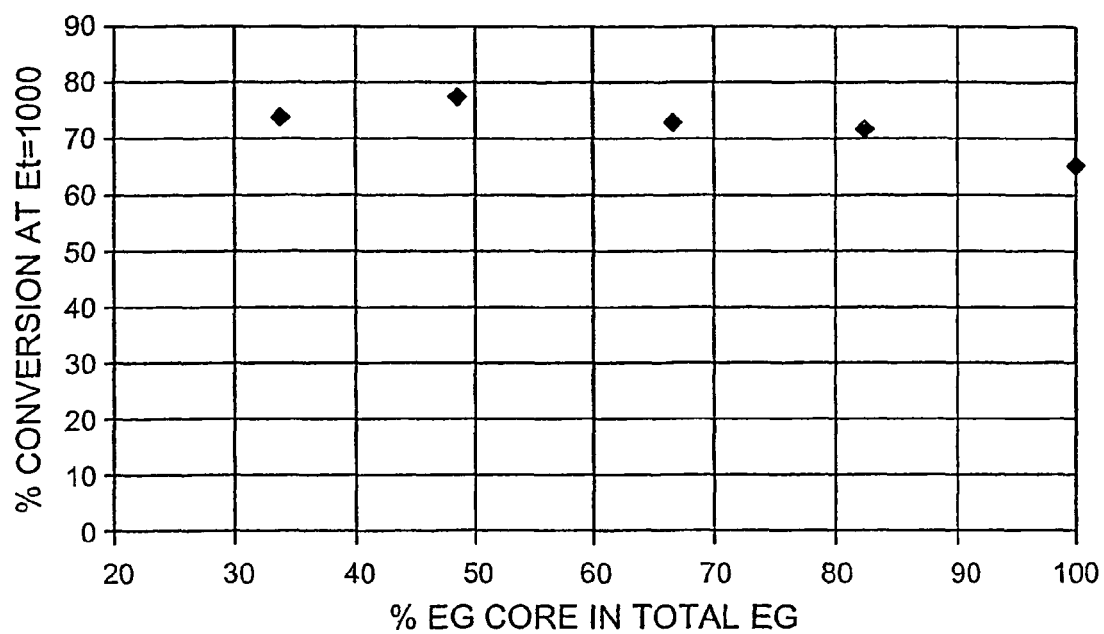
FIG. 1 shows a graphical representation of the effect of increasing the wt % of EGcore relative to the total EG in a cellulase mixture.

The present invention relates to the enzymatic conversion of cellulose to glucose. More specifically, the present invention provides a method for the conversion of pretreated lignocellulosic substrates using endoglucanase core protein, and the recovery and reuse of the endoglucanase core protein.

The following description is of a preferred embodiment by way of example only and without limitation to the combination of features necessary for carrying the invention into effect.

It is well known in the art that cellulose in many lignocellulosic materials may not be readily hydrolysable by enzymes. Thus, it is preferred that the cellulosic substrate for enzymatic hydrolysis as described herein be pretreated prior to being treated with enzymes.

There are a number of pretreatment processes known in the art that employ thermal, mechanical, chemical, or combinations of these methods to disrupt the fiber structure of cellulosic substrates and which enhance subsequent enzymatic hydrolysis of the cellulosic substrate. Any pretreatment process which enhances the enzymatic hydrolysis may be employed in combination with the method of the present invention. For example, but not wishing to be limiting, the pretreatment process disclosed in U.S. Pat. No. 4,461,648 or U.S. Pat. No. 4,237,226. (both of which are incorporated herein by reference) may be used, or any of the pulping processes known within the art (e.g. Rydholm S. A. 1985, Pulping Processes, Kreiger Pub. Co, which is incorporated herein by reference), including kraft, sulfite, mechanical, thermal, and chemi-thermal-mechanical pulping. Alternatively, pretreatment processes may also involve the addition of organic solvents to aid in the fractionation of lignin, cellulose and hemicellulose from lignocellulosic raw materials. These pretreatment processes may include but are not limited to those disclosed in U.S. Pat. No. 3,932,307 which teaches impregnating raw lignocellulosic material with a solution of lignin-solubilizing reactant in an organic solvent and subsequently immersing the impregnated material in a solvent that is neither soluble nor miscible with the reactant-containing solution with which the lignocellulosic material has been impregnated, U.S. Pat. No. 4,826,566, which uses solvent mixtures such as triethylene glycol with arylsulfonic or other acids; U.S. Pat. No. 5,859,236 which teaches impregnating lignocellulosic material with an extraction liquor containing a glycol and Lewis acid; and U.S. Pat. No. 5,730,837 which teaches treating lignocellulosic material with a combination of alcohol, water and water immiscible organic solvent, for example, a ketone.

A preferred pretreatment process is an acid-steam cook, as disclosed in U.S. Pat. No. 4,461,648, wherein an acid, for example sulfuric acid from about 0 to about 5%, is added to a lignocellulosic substrate, and the acidified mixture is cooked for about 5 seconds to about 2 minutes, at a temperature of about 180 to about 250° C.

Without wishing to be bound by theory, it is thought that the pretreatment process enhances subsequent enzymatic hydrolysis of cellulose by increasing delignification, creating micropores in the cellulose, changing the crystalline form of the cellulose, reducing the polymerization of cellulose, increasing the surface area of cellulose, or combinations thereof. As a large portion of the cellulose within many types of cellulosic substrate is normally unaccessible for enzymatic conversion to glucose without pretreatment, the efficiency of the pretreatment phase can influence the efficiency and commercial application of enzymatically converting cellulose to glucose.

By the term 'cellulosic substrate', it is meant any material comprising cellulose that maybe converted to glucose by enzymatic hydrolysis. The cellulosic substrate is preferably a pretreated lignocellulosic substrate, comprising at least about 10% lignin. For example, but not wishing to be limiting, the cellulosic substrate suitable for pretreatment may comprise:
  i) agricultural residues (lignin content about 15%) such as, but not limited to corn stover, wheat straw, barley straw, soybean stover;
  ii) residues following starch or sugar removal, for example but not limited to, oat hulls, rice hulls, corn fibre, sugar cane bagasse, sugar cane pulp;
  iii) dedicated ethanol crops, such as, but not limited to switch grass, miscanthus, cord grass, rye grass;
  iv) forestry products, for example, but not limited to hardwood (e.g. poplar; lignin content about 25%), softwood (lignin content about 35%), Eucalyptus, and forestry residues, sawdust; and
  v) other pretreated lignocellulosic substrates including pulp and paper products, for example but not limited to solka floc.

Pretreated hardwood, or agricultural residues, including corn stover, oat hulls barley straw or wheat straw cellulosic substrates produced by the method disclosed in U.S. Pat. No. 4,461,648 (which is incorporated herein by reference) are preferred lignocellulosic substrates.

Enzymatic hydrolysis of cellulose may follow pretreatment directly, or alternatively, a number of steps may follow pretreatment and precede enzymatic hydrolysis of cellulose. For example, but not wishing to be limiting, pretreated cellulosic substrate may be washed with water to remove chemicals, contaminants, or combinations thereof which could hinder the enzymatic conversion of cellulose to glucose.

By "exo-cellobiohydrolase" it is meant a protein comprising a cellulose binding domain, a linker region and a cellobiohydrolase (CBH) core region which acts at cellulose ends to release cellobiose. The cellulose binding domain can be linked to the cellobiohydrolase core region at either the N-terminal or C-terminal end of the cellobiohydrolase core region. The CBH may be obtained from any suitable organism. Preferably, the CBH is obtained from one or more of the following organisms: *Trichoderma, Hypocrea, Thermomonospora, Aspergillus, Streptomyces, Cellulomonas, Humicola, Fusarium, Fibrobacter, Clostridium, Bacillus*. More preferably, the CBH is obtained from *Trichoderma reesei*.

By "endoglucanase" or "EG" it is meant a protein comprising a cellulose binding domain, linker region and a endoglucanase core region which nicks cellulose polymers randomly to creating reducing and non reducing ends for digestion by exo-cellobiohydrolase. It is to be understood that the cellulose binding domain can be linked to the endoglucanase core region at either the N-terminal or C-terminal end of the endoglucanase core region. To date endoglucanase enzymes have been classified into several families (Table 1) based on amino acid similarities, 3 dimensional structural analysis and hydrolphobic cluster analysis (Henrissat et al., 1997, and 1998, and references therein). Endoglucanase therefore encompass a widespread group of enzymes that differ in molecular weight, amino acid sequence, and 3D-structure. For example the *Trichoderma reesei* EG2 protein (classified as a family 5 enzyme), is of approximately 50 kDa comprising a N-terminal cellulose binding domain, linker region and a EG2 core region and nicks cellulose polymers randomly creating reducing and non reducing ends for digestion by exo-cellobiohydrolase. The EG3 protein of *Trichoderma reesei* (a family 12 enzyme) is of 27 kDa and comprises a catalytic domain, and lacks a cellulose binding domain.

Preferably, the EG is obtained from one or more of the following organisms: *Trichoderma, Hypocrea, Thermomonospora, Aspergillus, Streptomyces, Cellulomonas, Humicola, Fusarium, Fibrobacter, Clostridium, Bacillus*. More preferably, the EG is obtained from *Trichoderma reesei*. However, it is to be understood that EG protein may be obtained from other sources as well, including but not limited to those listed in Table 1.

TABLE 1

Classification of known endoglucanases

| Family | Enzyme | Source |
|---|---|---|
| 5 | EG A | *Bacillus sp.* Strain N-4 |
|   | EG B | *Bacillus sp.* Strain N-4 |
|   | EG | *Bacillus lautus* |
|   | EG | *Bacillus subtilis* |
|   | EG | *Clostridium acetobutylicum* |
|   | EG A | *Clostridium celluloyticum* |
|   | EG B | *Clostridium thermocellum* |
|   | EGII | *Trichoderma reesei* |
|   | EG 5 | *Thermomonospora fusca* |
|   | EG | *Xanthomonas campestris* |
| 6 | EG A | *Cellulomonas fimi* |
|   | EG A | *Microbispora bispora* |
|   | EG A | *Streptomyces sp.* (KSM-9) |
|   | EG2 | *Thermomonospora fusca* |
| 7 | EGI | *Trichoderma reesei* |
| 8 | EG | *Cellulomonas uda* |
|   | EG A | *Clostridium thermocellum* |

TABLE 1-continued

Classification of known endoglucanases

| Family | Enzyme | Source |
|---|---|---|
| 9 | EG B | *Cellulomonas fimi* |
|   | EG C | *Cellulomonas fimi* |
|   | EG Z | *Clostridium stercorarium* |
|   | EG 4 | *Thermononospora fusca* |
| 12 | EG | *Aspergillus aculeatus* |
|   | EGIII | *Trichoderma reesei* |
|   | EG 3 | *Humicola Insolens* |
| 45 | EG 5 | *Humicola Insolens* |
|   | EG 5 | *Trichoderma reesei* |

By "endoglucanase core" it is meant the portion of endoglucanase comprising the catalytic domain of endoglucanase, and that is capable of endoglucanase activity as defined herein. An example of an endoglucase core, which is not to be considered limiting in any manner, is *Trichoderma* EG2core, which is approximately 38 kDa. EG2core may be isolated by from culture fitrates using chromatographic methods (Bhikhabhai, et al.; Stahlberg et al.). EG2core may also be produced by proteolytic cleavage of the EG2 protein using a suitable protease, for example but not limited to papain. One or more proteases, for example but not limited to papain, may also be added to a crude enzyme mixture to produce EG2core within the mixture. In this embodiment, depending on the protease added, other core enzymes may also be produced. EG2core may also be produced using recombinant technology. In this manner, EG2 and EG2 core may be co-expressed in the same host organism, or the host may be genetically modified so that the native EG2 expression is reduced or eliminated, and supplemented or replaced, respectively with recombinant EG2core expression. It is to be understood that endoglucanase core also includes fragments or derivatives of endoglucanase core, including substitutions, deletions, insertions within the endoglucanase core sequence as would be known to one of skill in the art, providing that these fragments and derivatives exhibit endoglucanase activity as described herein. It is also to be understood that endoglucanase core may be isolated from an organism wherein the endoglucanase core protein does not comprise a cellulose binding domain or linker region.

By the term "endoglucanase core plus linker" it is meant a fragment of a endoglucanase protein comprising endoglucanase core and the linker amino acid sequence, or a fragment thereof, that joins the endoglucanase core to the CBD of the endoglucanase protein. The linker portion of the endoglucanase core plus linker, may comprise any length of amino acid sequence. The endoglucanase core plus linker may include fragments or derivatives of endoglucanase core plus linker, including substitutions, deletions, insertions within the endoglucanase core plus linker sequence as would be known to one of skill in the art, providing that these fragments and derivatives of endoglucanase core plus linker exhibit endoglucanase core activity. The endoglucanase core plus linker may be isolated from an organism wherein the endoglucanase core plus linker protein does not comprise a cellulose binding domain, it may be prepared using recombinant techniques, or it may be prepared via proteolysis as would be known to one of skill in the art.

By the term "endoglucanase with inactive cellulose binding domain" it is meant a protein comprising endoglucanase core, or endoglucanase core plus linker, and a cellulose binding domain (CBD) that has been inactivated. Inactivation of a CBD may be performed by methods known in the art, for example but not limited to Linder et al. (Linder et al., 1995;

Linder et al., 1999, which are incorporated herein by reference). An inactivated CBD results in a reduced capacity of the CBD to bind cellulose when compared with the binding activity associated with a corresponding wild type endoglucanase. Further, it is to be understood that endoglucanase with inactive cellulose binding domain also includes fragments or derivatives of endoglucanase including substitutions, deletions, insertions within the endoglucanase, linker, CBD, or a combination thereof, sequence as would be known to one of skill in the art, providing that these fragments and derivatives exhibit endoglucanase activity, and exhibit a reduced capacity to bind cellulose. It is also to be understood that an endoglucanase with inactive cellulose binding domain may be isolated from an organism wherein the endoglucanase protein comprises a cellulose binding domain, however the CBD exhibits poor cellulose binding activity. An endoglucanase exhibiting poor cellulose binding activity exhibits less than about 70% of the cellulose binding activity of endoglucanase obtained from *Trichoderma reesei* using the same substrate. Preferably the endoglucanase exhibiting poor cellulose binding activity exhibits less than about 50% of the cellulose binding activity of *Trichoderma reesei* endoglucanase.

By "endoglucanase core protein" or "ECP", it is meant a protein comprising EG core, EG core plus linker, EG with inactive cellulose binding domain or native EG that lacks a CBD, for example but not limited to EG3, or a combination thereof. A endoglucanase core protein (ECP) is characterized as having endoglucanase core activity, along with a reduced or no, cellulose binding activity from the CBD.

Cellulase mixtures as described herein, may also comprise β-glucosidase (B-G). The β-glucosidase may be obtained form any suitable host, for example, but not limited to, *Trichoderma, Hypocrea, Thermomonospora, Aspergillus, Streptomyces, Cellulomonas, Humicola, Fusarium, Fibrobacter, Clostridium, Bacillus*, or a combination thereof. Preferably β-glucosidase is obtained from *Aspergillus*, or *Trichoderma*.

The present invention provides a method of converting cellulose within a cellulosic substrate into glucose comprising, treating a pretreated lignocellulosic substrate with an enzyme mixture comprising cellobiohydrolase, β-glucosidase, EG enzymes and endoglicanase core protein (ECP), wherein the EG enzymes comprise from 2 wt % to 50 wt % of the total of the CBH and EG enzymes (the amount of the B-G enzyme is not included in this determination) within the cellulase mixture present and wherein the ECP is present from 35 wt % to 0.100 wt % of all EG type enzyme.

No significant loss in activity is observed using a cellulase mixture as described above, where all the endoglucanase is replaced with endoglucanase core (FIG. 1). Preferably the ECP is from about 50 to 90 wt % of the EG type enzyme, and more preferably from about 60 to 80 wt %. It is also preferred that the endoglucanase core protein is a *Trichoderma* endoglucanase.

The present invention also provides a cellulase composition comprising CBHI, CBHII, EG I, EG II, EGIII, β-glucosidase and endoglucanase core protein wherein the ECP is present in the cellulase composition at an amount relative to all EG type enzyme of from about 35 to about 100 wt %. Preferably the ECP is from about 50 to about 90 wt % of the EG type enzyme, and more preferably from about 60 to 80 wt %. It is also preferred that the ECP is a *Trichoderma* endoglucanase. In this embodiment, the endoglucanase core protein may be added to a cellulase mixture (comprising one or more of CBHI, CBHII, EG I, EG II, EGIII and β-glucosidase) produced by, for example, but not limited to a filamentous fungus. Preferably, the filamentous fungus is *Trichoderma*. Similarly, endoglucanase core protein may be expressed by a host capable of producing a cellulase enzyme mixture (comprising CBHI, CBHIII, EG I, EG II, and β-glucosidase).

The present invention, also provides a method for converting cellulose to glucose comprising CBHI, CBHII, EG I, EG II, and EGIII, β-glucosidase and endoglucanase core protein wherein the ECP, for example EG core plus linker, is present in the cellulase composition at an amount relative to all EG type enzymes of from about 35 to about 100 wt %. Preferably the EG core plus linker is from about 50 to about 90 wt % of EG type enzymes, and more preferably from about 60 to about 80 wt %. It is also preferred that the EG core plus linker is a modified *Trichoderma* EG.

Further contemplated by an aspect of an embodiment of the present invention there is provided a method for converting cellulose to glucose using an enzyme mixture comprising CBHI, CBHII, EG I, EG II, EGIII, β-glucosidase and endoglucanase core protein wherein the endoglucanase core protein, for example EG core with an inactivated cellulose binding domain is present in the cellulase composition at an amount relative to all EG type enzymes of from about 35 to about 100 wt %. Preferably the EG core plus linker is from about 50 to about 90 wt % of the EG type enzyme, and more preferably from about 60 to about 80 wt %. It is also preferred that the EG with an inactivated binding domain is from *Trichoderma*, Inactivation of the EG CBD may be accomplished using any suitable method as would be known within the art, for example but not limited to the method of Linder (Linder et al., 1995 and 1999; which are herein incorporated by reference). These references describe changes to single amino-acids within the CBD that result in partial or complete loss in the capacity for the CBD to bind cellulose. Other methods for inactivation of the CBD may include deletion of a portion of the CBD, or insertion of a peptide sequence within the CBD in order to disrupt CBD binding activity.

Persons skilled in the art are aware that cellulose hydrolysis may occur under a variety of conditions. Preferably, cellulose hydrolysis is performed by cellulase enzymes in a slurry of water and cellulase comprising about 1 to about 25 wt % lignocellulosic solids at a pH of about 4 to about 5 and at a temperature of about 50° C. At concentrations of less than wt % lignocellulosic solids the solution of glucose obtained is dilute is typically concentrated for further processing. While this step of concentration may be performed, it is not a preferred method. At high cellulose concentrations above 25 wt % lignocellulosic solids, the solids content in the reaction may become difficult to mix, filter and process. Persons skilled in the art are aware that lignocellulosic materials after pretreatment can possess a range of cellulose content, therefore the amount of lignocellulosic material that is required to achieve a desired cellulose concentration can vary. It is preferred that the amount of pretreated lignocellulosic substrate is from about 10 wt % to about 16 wt %. A more preferred amount of pretreated lignocellulosic substrate is from about 12 wt % to about 16 wt %. These conditions are suitable for most cellulase enzymes; However, the present invention also contemplates hydrolysing cellulose under other conditions that may be better suited to a particular cellulase/EG core, EG-EG core, or other mixtures comprising EG core protein as defined herein. Such conditions may be readily determined by one of skill in the art.

Also included in the present invention is a cellulase composition comprising CBHI, CBHII, EG I, EG II, EGIII, β-glucosidase and endoglucanase core protein, wherein the EG enzyme is present in the cellulase composition from about 2 wt % to 50 wt % relative to the amount of CBH and EG present Persons skilled in the art are aware that the CBH and EG enzymes act synergistically. Below 2 wt % of EG relative to the total CBH and EG enzymes, the amount of EG may be too low to result in effective hydrolysis. As the amount of EG increases relative to CBH the observed performance is increased. The efficiency of cellulose conversion is much higher for CBH enzymes compared to EG enzymes, therefore it is preferred that the cellulase mixture contain at least about 50% CBH. It is also understood that the relative amount of CBH1 and CBH2 can vary from 25 wt % to 95 wt % of CBH1. Those skilled in the art are aware that CBH1 and CBH2 also act synergistically to hydrolyse cellulose to glucose, and the activity of the enzymes in combination is greater than the sum of the individual activities.

Any source of cellulase enzyme system may be used in accordance with the method of the present invention. Preferably, cellulase enzymes, are from *Trichoderma longibrachiatum*, and *Trichoderma reesei*, or a combination thereof. Furthermore, the EG and EG core protein, for example but not limited to EG2 core, proteins are also preferably obtained from *T. longibrachiatum*, and *T. reesei*, or a combination thereof.

The crude *Trichoderma* cellulase enzymes used as a basis for in the method of the present invention may be obtained directly through culture of the appropriate microorganism, or the enzymes may be purchased commercially (e.g. from Iogen Corporation). EG core protein may be obtained by expressing the appropriate genetic sequence in an suitable host cell, as is commonly performed in the art, and as described in U.S. Pat. No. 5,874,276 (which is incorporated herein by reference) or EG core protein may be prepared by enzymatic cleavage of EG as described above. Similarly, EG core plus linker may be obtained by expressing a nucleotide sequence comprising the EG core and linker region, or via proteolytic cleavage of the holoenzyme. EG with an inactive cellulose binding domain may be obtained as described above, by expressing the appropriate gene sequence encoding an inactive CBD either through substitution, deletion or insertion, or as would be known by one of skill in the art.

The skilled practitioner will realize that the amount of cellulase enzyme to be used in the hydrolysis of cellulose to glucose may be determined by the nature of the cellulosic substrate, the pretreatment process, the cost of the enzymes, the desired hydrolysis time, and the desired glucose yield from the cellulosic substrate. A typical enzyme dosage range is about 1 to about 50 Filter paper units (FPU) cellulase per gram cellulose for a period of time from about 3 to about 200 hours. In a preferred embodiment the cellulase enzyme dosage is from about 1 to about 10 FPU per gram cellulose.

The skilled practitioner is aware that the cellulose concentration is chosen to accommodate the capabilities of pumps to handle and mix the solids. Depending on the material, a pretreated lignocellulosic substrate concentration to be used in the hydrolysis of cellulose to glucose is from about 1 wt % to about 25 wt % is used. The preferred amount of pretreated lignocellulosic substrate is from about 10 wt % to about 16 wt %. A more preferred amount of pretreated lignocellulosic substrate is from about 12 wt % to about 16 wt %.

FIG. 1 shows the relative activity of a cellulase mixture as the percent of endoglucanase core protein is increased relative to the total endoglucanase enzyme in the mixture. The cellulase mixture used in this experiment, which is not to be considered limiting in any manner, contains 18 wt % endoglucanase enzyme relative to the EG and CBH enzymes present. The amount of endoglucanase core protein was varied from the maximum reported percentage found in *Trichoderma* (33 wt %) to 100 wt %. When the amount of endoglucanase core protein is increased relative to total endoglucanase enzyme in the mixture from 33 to 100%, only a small loss in hydrolysis activity is observed. The enzyme activity can be compared using a fixed Et and comparing the percentage conversion of cellulose.

Et is defined as the enzyme concentration in mg of cellulase per g of cellulose multiplied by the time in hours for the reaction. Using this analysis at Et=1000 (mg/g)hr (see Example 1, Table 2, and FIG. 1) only 13% activity less was observed when 100% endoglucanase core protein was present in the enzyme mixture when compared with the Et observed with 33% ECP in the EG mixture.

Figure 2A:
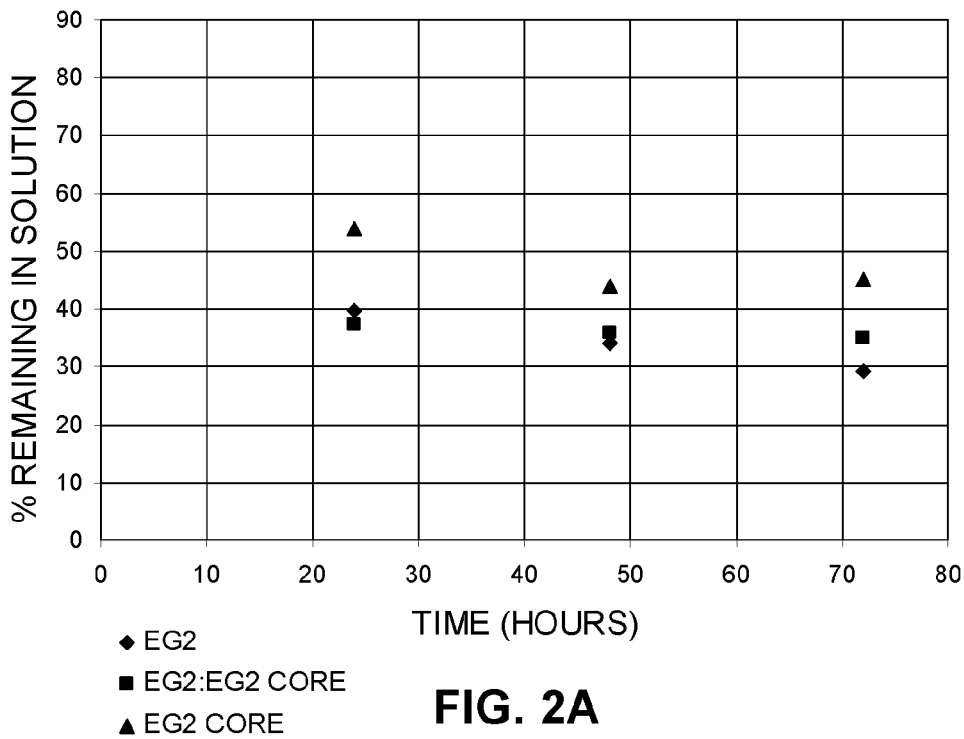
FIG. 2A shows that for pretreated whole oats after 24, 48 and 72 hours of hydrolysis EG2 core is more soluble than EG2 throughout the hydrolysis reaction. Approximately 30 to 85% more EGcore than EG2 remains in solution after hydrolysis.

As increasing the relative amount of endoglucanase core protein does not decrease the activity of the cellulase mixture (FIG. 1), the ability to recover EG2 core relative to EG2 was examined. As shown in FIG. 2A, the amount of EG2 core remaining in solution, following a partial recovery of protein was greater than that of EG2 by 30 to 85% during the hydrolysis of a pretreated lignocellulosic material. During hydrolysis of Sigmacell™ more than two fold the amount of ECP remained in solution compared with EG2. EG core protein, for example but not limited to EG2core may be more easily recovered than EG2, and this attribute may be advantageous in cellulose hydrolysis.

Referring now to FIG. 3 there is shown a summary of the relative activity of EG2 and EG2 core, which was observed to be similarly stable over 15 to 20 days at 50 C and pH 4.8. This attribute may be advantageous in the recovery and reuse of enzymes in cellulose hydrolysis.

Enzyme remaining in solution after hydrolysis may be recovered using standard techniques as known within the art. For example, which is not to be considered limiting in any manner, the solids fraction may be removed from a reaction mixture, by filtration or centrifugation, and the protein remaining in solution may be separated from the sugar liquor and recovered via ultrafiltration, or precipitation, including pH, salting-out, or temperature induced precipitation.

Therefore, this invention is directed to the hydrolysis of cellulosic substrates using a cellulase mixture containing an endoglucanase core protein (ECP), for example but not limited to EG2 core protein, that is characterized by having a low tendency to bind to cellulosic substrates, but still exhibits high activity.

The present invention also pertains to a method for the hydrolysis of a cellulosic substrate comprising adding a sufficient amount of ECP, for example but not limited to EG2 core, to a cellulase enzyme mixture and allowing the reaction to proceed for a period of time sufficient to hydrolyze cellulose to glucose.

The present invention provides for a method for the hydrolysis of a cellulosic substrate using a cellulase mixture containing an ECP, for example but not limited to EG2 core protein, over a range of mixtures from about 35 wt % to 100 wt % relative to the total EG in the enzyme mixture.

The above description is not intended to limit the claimed invention in any manner. Furthermore, the discussed combination of features might not be absolutely necessary for the inventive solution.

The present invention will be further illustrated in the following examples. However, it is to be understood that these examples are for illustrative purposes only, and should not be used to limit the scope of the present invention in any manner.

Example 1

Hydrolysis of Enzymes Mixtures with Varying Levels of EG Core

The substrate used is whole oats as per U.S. Pat. No. 4,461,648; pretreatment process involved adding sulphuric acid from about 0 to 5% to the whole oats and the acidified mixture cooked for about 5 seconds to about 2 minutes, at a temperature of about 180 to about 250° C. The cellulose content of the pretreated material is 50%.

Purified CBH1 and CBH2 was obtained from a crude *Trichoderma* cellulase broth by first filtering the broth through glass microfiber filter paper. The cellulase liquid was then dialyzed using a 10,000 MW cut off membrane in order to lower its conductivity to 12,000 µS. The CBH1 was enriched by loading 190 mg protein/mL of resin onto pH 6 DEAE Sepharose ion exchange resin. The other components were desorbed from the resin before CBH1, by running 50 mM phosphate, 25 NaCl buffer at a conductivity of 9,000 µS throught the column. The CBH1 was desorbed by running 50 mM phosphate, 300 mM NaCl buffer at a conductivity of 30,000 µS through the column. The CBH1 was then concentrated by ultrafiltration and its purity was accessed by a LKB Bromma iso-electrofocusing electrophoresis unit.

CBH2 was purified by dialyzing to 700 µS and loading the CBH1 deleted mixture obtained above onto an S Sepharose ion exchange resin equilibrated with pH acetate buffer. CBH2 was enriched by collecting the loosely bound proteins collected at a conductivity of 1300 µS. The enriched CBH2 mixture was dialized into pH 4 acetate buffer and passed through a CM-sepharose column. CBH2 was desorbed from the column using a 6 mM acetate, 40 mM NaCl buffer at a conductivity of 5100 µS. The CBH2 purity was accessed by iso-electrofocusing.

EG1 and EG2 and EG3 were obtained by collecting the unbound proteins from the S sepharose column described above. Alternatively an EG, EG2 and EG3 enriched culture can be obtained from a *Trichoderma* strain deleted in CBH1 and CBH2. Using the anion exchange resin PBE 94 and a 12.5% solution of polybuffer 74 a pH gradient from pH 4 to pH 7 was generated using 0.025 M pH 7.4 imidazole buffer allowing EG1 and EG2 to be separated using chromatofocusing methods. EG2 (pI=5.3) is eluted prior to EG1 (pI=4.6). Purity was accessed by SDS page and capillary isoelectrophoresis on a PAGE Beclman MDQ capillary electrophoresis instrument.

EG2core was obtained using a *Trichoderma* strain enriched in EG2core using a short thermal purification (pH 5.1, 60C, 4 hrs) followed by a chromatofocusing step using a pH 4 to 7 gradient, PBE94 anion exchange resin and a 12.5% solution of polybuffer 74 as described above. Purity was accessed by SDS page and capillary isoelectrophoresis.

Hydrolysis reactions contained 5% cellulose in 50 mM pH 4.8 citrate buffer to a total weight of 2.5 gms. 116 IU β-glucosidase per gram cellulose was added to each tube. For each reaction five dosages of enzyme mixture, 6.25, 12.5, 25, 50, 75 mg of enzyme/gram of cellulose was prepared. Each dosage was composed as described by the wt % in Table 2. The mixtures were combined in the ratio of 18% endoglucanase protein relative to the amount of CBH and EG enzyme. Starting from an initial composition of 33% endoglucanase core protein relative to the total endoglucanase protein the percent of EG core protein was increased to 100%. The mixtures were incubated at 50C with shaking at 250 RPM for 20 hrs. At this time the mixture was filtered through glass microfiber filter paper. The amount of remaining cellulose in the reaction was measured by converting the polymeric cellulose to glucose using acid hydrolysis and measuring the glucose using a glucose oxidase/horseradish peroxidase coupled assay (Bauminger, 1974).

A cellulase mixture can be prepared from individual components in two ways. In this experiment the cellulase components are combined using a wt % ratio where the wt % of the individual component is calculated relative to the total cellulase mixture composed of CBH1, CBH2, EG1, EG2, and EG3. β-Glucosidase is added in excess (116 IU/g cellulose) to this mixture. The cellulase components may also be mixed using a molar ratio. For example, Schulein combined the *Humicola insolen* CBH1 and EGV in a molar ratio of 90:5. Given that the molecular weight of these two components are 72 kD and 30 kD respectively, this molar ratio corresponds to a 2.3 wt % of endoglucanase to the amount of CBH and EG. Given that EGVcore has a molecular weight of 22 kDa, a 90:5 molar ratio of CBH1 to EGVcore would correspond to a wt % of endoglucanase core protein to the total CBH and EG enzyme of 1.7%.

The amount of cellulose conversion at a fixed Et of 1000 was determined for each enzyme mixture (Table 2) where Et is defined as the product of enzyme concentration in mg of enzyme/g of cellulose multiplied by the time in hours for the reaction. The relative activity of the enzymes mixture as a function of the EG core composition is listed in Table 2 and shown graphically in FIG. 1. It can be seen that the activity remains constant when the amount of endoglucanase core protein is increased from 33 wt % to 80 wt %. A small decrease in activity, of about 13%, is observed on increasing the endoglucanase core protein from 80 wt % to 100 wt % relative to the total endoglucanase core protein.

TABLE 2

Relative activity with increasing endoglucanase core concentration in a cellulase mixture*

| EG (% of total cellulase) | % core in EG mix | % conversion at Et = 1000 (mg/g) hrs | Relative activity |
|---|---|---|---|
| EG1(6):EG2(6):EG3(6) | 33 | 74.2 | 1.00 |
| EG1(6):EG2(3):EG2core(3): EG3(6) | 50 | 77.2 | 1.04 |
| EG1(6):EG2core(6):EG3(6) | 67 | 73.5 | 0.99 |
| EG1(3):EG2core(7):EG3(8) | 83 | 71.7 | 0.96 |
| EG2core(9):EG3(9) | 100 | 65.0 | 0.87 |

*total cellulase mixture consists of 76% CBH1, 6% CBH2, 18% EG, and 116 IU β-G per g cellulose.

These data demonstrate that endogluconase core protein is active over a range of the amount of EG core protein (ECP) within the EG type enzyme composition.

Example 2

Recovery of Protein from Solution Following Hydrolysis

As described above three separate 5% cellulose hydrolysis reactions in 50 mM pH 4.8 citrate buffer containing EG2, EG2:EG2core (in 50 wt % ratio) and EG2core were prepared. After a 24, 48 and 72 hours of incubation at 50 C the reaction mixtures were filtered to remove remaining solids, and amount of protein remaining in solution from the reaction was measured.

Protein measurement was done using a Biorad protein assay using a commercial product Iogen Cellulase (90 g/L) as a standard. The results are shown in Table 3. The two substrates analyzed were oats hulls and Sigmacell™.

TABLE 3

Protein remaining in solution following hydrolysis

| Substrate/Enzyme | % Recovery of Protein | | |
|---|---|---|---|
| | 24 hrs | 48 hrs | 72 hrs |
| Oat Hulls | | | |
| EG2 | 39.6 | 34.1 | 29.1 |
| EG2:EG2core | 37.4 | 36.0 | 37.4 |
| EG2core | 53.9 | 43.8 | 53.9 |
| Sigmacell | | | |
| EG2 | 38.5 | 41.2 | 38.4 |
| EG2:EG2core | 70.9 | 56.0 | 70.9 |
| EG2core | 85.1 | 76.8 | 85.1 |

Figure 2B:
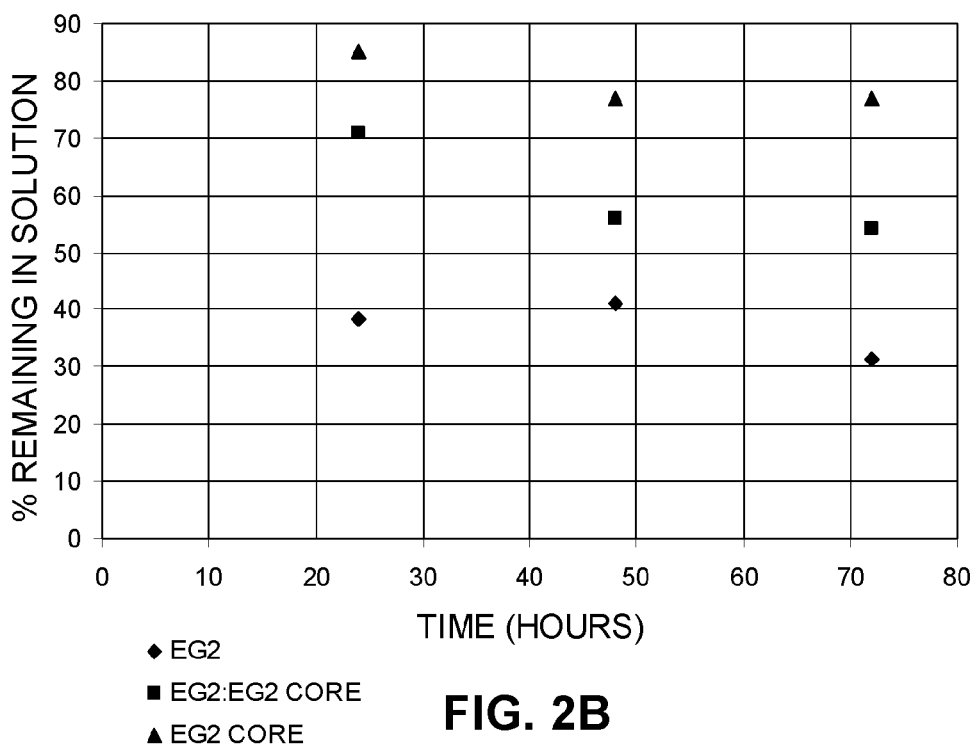
FIG. 2B shows that more EG2core remains in solution that EG2, using Sigmacell™ as a substrate, under the same conditions.

The amount of EG2core in solution throughout the course of hydrolysis is higher than the amount of EG2. Approximately 30 to 85% more EG2core than EG2 could be detected in solution after hydrolysis. This was observed with both a high surface area lignocellulosic substrate such as whole oats or Sigmacell™. These results are shown graphically in FIGS. 2A and 2B. Given that EG2 core is as efficient as EG2 in a cellulase mixture as described herein, the use of EG2core offers the opportunity to be recovered and reused. It is also observed that the amount of protein remaining in solution is substrate dependant and without wishing to be bound by theory may be dependant on the amount on lignin present in the lignocellulosic substrate.

At the end of a hydrolysis reaction, enzymes that remain in solution may be recovered from the reaction mixture by removing the unreacted solids by filtration, and separating and recovering the enzymes from the sugar liquor using ultrafiltration. The enzyme may also be recovered by precipitation from the sugar liquor, for example by pH, salt, or temperature-induced precipitation.

Example 3

Stability of EG2 and EG2 Core in Solution

The stability of purified EG2 and EG2core was assessed under the typical conditions of hydrolysis. The enzymes were incubated at a concentration of 2.4 mg/mL and 2.9 mg/mL respectively in a pH 4.8 citrate buffer at 50° C. Aliquots were removed and the level of Carboxymethylcellulose (CMC) hydrolysis was assessed by quantification of reducing sugars using DNS.

The results are shown in FIG. 3. Both EG2 and EG2core were found to be equally stable. Given that EG2core is equally stable and equally active in an cellulase enzyme mixture as described herein and also more recoverable than EG2 it offers the opportunity to be recovered and reused.

Example 4

Method for Determining the Percentage of EG and EGcore Protein in a Cellulase Mixture Trichoderma cellulase mixtures, made by strain RUT-C30 (available from the ATCC #56765) were analyzed for composition. The CIEF determinations were conducted on a. PAGE 5000 instrument. Separations were carried out using a Beckman eCAP neutral capillary (ID 50 µM×OD 365 µM, 27 cm in length). The cellulase standards or cellulase extracts were dissolved to their final concentration in an aqueous solution consisting of 3% blended carrier ampholyte (Beckman ampholyte: Servalyt (3:1, v/v)). The analyte was 10 mM phosphoric acid and the catholyte was 20 mM NaOH. A Voltage of 13.5 kV was used to focus the analyte band for a duration of 10 min followed by cathodic mobilization using a buffer of methanol water-acetic acid (50:49:1, v/v/v). During focusing and mobilization, the voltage was maintained at a field strength of 13.5 kV (500 V/cm). The detector was set at 280 nM. Protein concentrations of standards and Trichoderma secreted cellulase mixtures were based on Bradford determination.

Under these conditions, migration times for CBH1, CBH2, EG1, EG2, and EG3 are 31, 23, 29, 28 and 22 minutes respectively. Migration times can vary by about ±1 min but the identity of the peaks is confirmed using internal standards. Identity of peals in a mixture is confirmed by spiking in four internal standards (myoglobin, pI 6.8, 7.2—two isoforms), β-lactoglobulin A (pI=5.1) and CCK flanking peptide (pI 2.75) providing four points for a calibration curve. pI and identity of individual peaks is confirmed by calculating the pI of the peak using the retention time versus pI calibration curve of the standards.

The percentage of EG relative to the total EG and CBH present is calculated to be 8% in RUT-C30 (see Table 4). The percent EG is determined using the ratio of EG protein to the total EG and CBH enzymes comprising of CBH1, CBH2, EG1, EG2 and EG3. The percentage of endoglucanase core in the cellulase extract is calculated from the amount of EG3 relative to the total amount of endoglucanase protein. EG1core and EG2core were not observed in the cellulase mixture, therefore, the amount of EG core protein in the extract from RUT-C30 is 0.

TABLE 4

Distribution of cellulases in secreted protein extracts obtained from Trichoderma reesei.

| Cellulase Protein (µg/mL) | RUT-C30 |
|---|---|
| CBH1 | 169.3 ± 2.1 |
| CBH1 core | n.o. |
| CBH2 | 8.1 ± 0.2 |
| EG1 | 7.0 ± 0.6 |
| EG1 core | n.o. |
| EG2 | 8.2 ± 0.6 |
| EG2 core | n.o. |
| EG3 | n.o. | n.o. none observed

All citations are herein incorporated by reference.

The present invention has been described with regard to preferred embodiments. However, it will be obvious to persons skilled in the art that a number of variations and modifications can be made without departing from the scope of the invention as described herein.

REFERENCES

Bissett, F. H., (1979) J. Chrom. 178, 515-523
Bauminger, B. B., J. Clin. Pathol. 27, (1974) p 1015
Bhikhabhai, R. et al., (1984) J. App. Biochem. 6, 336-345
Fan et al., Evaluation Of Pretreatments For Enzymatic Conversion Of Agricultural Residues, Proceedings of the Third Symposium on Biotechnology in Energy Production and Conservation, (Gatlinburg, Tenn., May 12-15, 1981).
Gile's et al., (1992) J. Biol. Chem, 267, 6743-6749
Grethlein and Converse (1991) Bioresource Technology 36 (2), 77-82

Grohmann, et al, Optization of Dilute Acid Pretreatment of Biomass, Seventh Symposium on Biotechnology for Fuels and Chemicals (Gatlinburg, Tenn., May 14-17, 1985)
Henrissat et al., (1997) *Curr. Opinl.* 7, 637-644
Henrissat et al., (1998) *FEBS Lett.* 425, 352-354
Hui J. et al., (2001) *J. Chrom. B.* 752, 349-368
Hui J. (2001) MSc Thesis, University of Ottawa
Kotiranta, P et al., (1999) *App Biochem. Biotech.* 81, 81-90
Linder et al (1995) *Prot. Sci.* 4, 1056-1064
Linder et al (1999) *FEBS Lett.* 447, 13-16
Macarron, et al., (1995), *Biochim. Biophys. Acta,* 1245, 187-190
Knappert, et al., (1980) *Biotech. and Bioeng.* 23, 1449-1463
Nidetzlcy et al., (1994) *Biochem. J.* 303, 817-823
Penttila, M. et al., (1986) Gene 45, 253-263
Saloheimo, M et al., (1988) Gene 63, 11-21
Schulein M. Proceedings from CIFAR Conference XIV, UC Davis, Jun. 4, 2001
Shoemaker et al., (1983) Bio/Technology 1, 691-696
Stahlberg et al., (1988) *Eur. J. Biochem.* 173, 179-183
Teeri et al., (1987) Gene 51, 43-52
Teeri et al., (1992) *J. Biotech.* 24, 169-176
Teeri, T. T. and Koivuval A. (1995) *Carbohydr. Eur.* 12, 28
Tomme et al., (1988) *Eur. J. Biochem* 170, 570-581

The embodiments of the invention in which an exclusive property or privilege is claimed are defined as follow:

1. A method of converting the cellulose within a lingocellulosic substrate to glucose, comprising the steps of:
    pretreating a lignocellulosic substrate comprising at least about 10% lignin by chemical action so as to hydrolyze hemicellulose contained therein, thereby producing a chemically pretreated lignocellulosic substrate;
    treating said chemically pretreated lignocellulosic substrate with an enzyme mixture comprising cellobiohydrolase (CBH) enzymes, β-glucosidase enzymes, and endoglucanase (EG) enzymes for a sufficient time and under conditions suitable for converting at least about 65% of the cellulose within said lingocellulosic substrate to glucose, wherein said EG enzymes are present at an amount from about 2 to about 50 wt % relative to total amount of CBH enzymes and EG enzymes present in the enzyme mixture, and wherein from about 35 to about 100 wt % of said EG enzymes is a fungal EGII enzyme catalytic core domain; and
    recovering said fungal EGII catalytic core domain following said step of treating,
    wherein the lignocellulosic substrate is selected from the group consisting of corn stover, wheat straw, barley straw, soybean stover, oat hulls, rice hulls, sugar cane bagasse, corn fibre, switch grass, miscanthus, cord grass, rye grass, hardwood, softwood, Eucalyptus and sawdust, or combination thereof.

2. The method of claim 1, wherein said EG enzymes are present in said enzyme mixture in an amount from 7 to 30 wt % relative to the total amount of CBH enzymes and EG enzymes present in the enzyme mixture.

3. The method of claim 1, wherein said fungal EGII catalytic core domain is present in said enzyme mixture at from about 50 to about 90 wt % of said EG enzymes.

4. The method of claim 3, wherein said fungal EGII catalytic core domain is present in said enzyme mixture at from about 60 to about 80 wt % of said EG enzymes.

5. The method of claim 1, wherein said fungal EGII catalytic core domain comprises a linker.

6. The method of claim 1, wherein the β-glucosidase enzymes, in said enzyme mixture are obtained from at least one of *Trichoderma, Hypocrea, Thermomonospora, Aspergillus, Streptomyces, Cellulomonas, Humicola, Fusarium, Fibrobacter, Clostridium,* or *Bacillus.*

7. The method of claim 6, wherein the CBH and EG enzymes in said enzyme mixture are obtained from *Trichoderma,* and said β-glucosidase enzymes are obtained from *Aspergillus* or *Trichoderma.*

8. The method of claim 7, wherein said CBH enzymes and EG enzymes are from *Trichoderma reesei.*

9. The method of claim 1, wherein said fungal EGII catalytic core domain is reused to hydrolyze cellulose following said step of recovering.

10. The method of claim 1, wherein said lignocellulosic substrate is selected from the group consisting of corn stover, wheat straw, barley straw, and soybean stover.

11. The method of claim 1, wherein the pretreated lignocellulosic substrate is present at a concentration of about 1 to about 25 wt % when treated with said enzyme mixture.

12. The method of claim 10, wherein said lignocellulosic substrate is present at a concentration of about 10 to about 16 wt % when treated with said enzyme mixture.

13. The method of claim 1, wherein said step of recovering comprises precipitating said fungal EGII catalytic core domain, or using an ultrafiltration membrane to recover said fungal EGII catalytic domain from solution.

14. The method of claim 1, wherein said pretreating comprises an acid steam cook.

15. The method of claim 1, wherein said CBH enzymes comprise Cellobiohydrolase I (CBHI) and Cellobiohydrolase II (CBHII).

16. The method of claim 15, wherein CBHI is present from about 25 to about 95 wt % of said CBH enzymes.

17. The method of claim 15, wherein the CBHI is from *Trichoderma.*

18. The method of claim 15, wherein the CBHII is from *Trichoderma.*

19. The method of claim 1, wherein said lignocellulosic substrate is selected from the group consisting of oat hulls, rice hulls, sugar cane bagasse and corn fibre.

20. The method of claim 1, wherein said lignocellulosic substrate is selected from the group consisting of switch grass, miscanthus, cord grass and rye grass.

21. The method of claim 1, wherein said lignocellulosic substrate is selected from the group consisting of hardwood, softwood, Eucalyptus and sawdust.

* * * * *

UNITED STATES PATENT AND TRADEMARK OFFICE
CERTIFICATE OF CORRECTION

PATENT NO. : 8,012,721 B2
APPLICATION NO. : 10/507618
DATED : September 6, 2011
INVENTOR(S) : Daphne Wahnon et al.

It is certified that error appears in the above-identified patent and that said Letters Patent is hereby corrected as shown below:

ON THE TITLE PAGE Item [56] (page 1, right column) REFERENCES CITED:

Other Publications, Line 2, "Lawford et la.," should read --Lawford et al.,--.

ON THE TITLE PAGE Item [56] (page 2, left column) REFERENCES CITED:

Other Publications, Line 15, "Suumakki" should read --Suurnäkki--.

ON THE TITLE PAGE Item [56] (page 2, right column) REFERENCES CITED:

Other Publications, Line 13, "Cromatography" should read --Chromatography--.

ON THE TITLE PAGE Item [56] (page 2, right column) REFERENCES CITED:

Other Publications, Line 19, "Family a" should read --Family A--.

ON THE TITLE PAGE Item [56] (page 2, right column) REFERENCES CITED:

Other Publications, Line 24, "endocellulasese" should read --endocellulases--.

ON THE TITLE PAGE Item [56] (page 3, right column) REFERENCES CITED:

Other Publications, Line 29, "Collen et al.," should read --Collén, et al.,--.

ON THE TITLE PAGE before Item (74) Attorney, Agent, or Firm:

Please insert, --Supervisory Examiner—Michael Wityshyn--.

Signed and Sealed this
Fourth Day of September, 2012

David J. Kappos
*Director of the United States Patent and Trademark Office*

IN FIGURE SECTION (After FIG. 2B) INSERT:

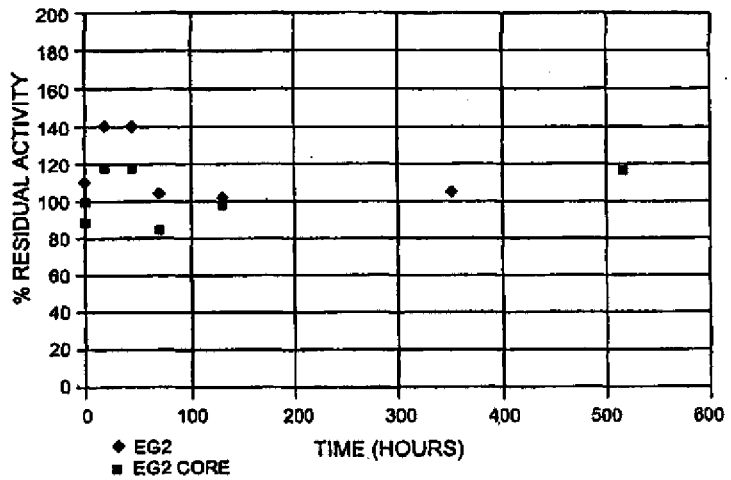

FIG. 3

COLUMN 1:

Line 26, "cellooligosaccha-" should read --cello-oligosaccha- --;
Line 44, "CBH II" should read --CBHII--; and
Line 48, "CBH II" should read --CBHII--.

COLUMN 2:

Line 11, "substrates" should read --substrate--;
Line 13, "Nidetzcy" should read --Nidetsky--;
Line 17, "Nidetzly" should read --Nidetsky--;
Line 30, "endoglucanasev" should read --endoglucanase V--;
Line 59, "1980, both" should read --1980 (both--; and
Line 60, "reference In" should read --reference). In--.

COLUMN 3:

Line 16, "cost and" should read --cost, so as to--; and
Line 35, "back" should read --backs--.

COLUMN 4:

Line 29, "CBHI, CBHI," should read --CBHI, CBHII,--;
Line 37, "method" should read --methods--;
Line 51, "CBH, CBHI," should read --CBHI, CBHII,--; and
Line 61, "CBHI, CBHI," should read --CBHI, CBHII,--.

CERTIFICATE OF CORRECTION (continued)
U.S. Pat. No. 8,012,721 B2

COLUMN 5:

Line 1, "is" should be deleted;
Line 4, "is" should be deleted;
Line 11, "invention but that" should read --invention, rather--;
Line 25, "EG2 core" should read --EG2core--;
Line 29, "that EG2" should read --than EG2--;
Line 34, "EG2 core" should read --EG2core--; and
Line 62, "U.S. Pat. No. 4,237,426." should read --U.S. Pat. No. 4,237,426--.

COLUMN 6:

Line 25, "wishing to be bound by theory," should read --being limited,--;
Line 38, "maybe" should read --may be--;
Line 41, "wishing" should read --meant--;
Line 58, "Pretreated" should read --or combinations thereof. Pretreated--;
Line 59, "oat hulls" should read --oat hulls,--; and
Line 66, "wishing" should read --meant--.

COLUMN 7:

Line 16, "and a endo-" should read --and an endo- --;
Line 18, "creating" should read --create--;
Line 26, "hydrolphobic" should read --hydrophobic--;
Line 28, "encompass" should read --encompasses--;
Line 32, "a N-terminal" should read --an N-terminal--; and
Line 33, "a EG2 core" should read --an EG2core--.

COLUMN 8:

Line 21, "by from culture fitrates using" should read --from culture filtrates by using--;
Line 30, "EG2 core" should read --EG2core--;
Line 38, "providing" should read --provided--; and
Line 45, "of a endoglucanase" should read --of an endoglucanase--.

COLUMN 9:

Line 32, "form" should read --from--;
Line 41, "endoglicanase" should read --endoglucanase--; and
Line 46, "0.100 wt %" should read --100 wt %--.

COLUMN 10:

Line 25, "choderma," should read --choderma.--;
Line 29, "amino-" should read --amino--;

Line 40, "less than wt" should read --less than 1 wt--;
Line 42, "dilute is" should read --dilute and is--;
Line 55, "enzymes," should read --enzymes.--; and
Line 66, "present Persons" should read --present. Persons--.

COLUMN 11:

Line 22, "in" should be deleted; and
Line 53, "is used" should be deleted.

COLUMN 12:

Line 12, "EG2 core" should read --EG2core--;
Line 13, "EG2 core" should read --EG2core--;
Line 17, "two fold" should read --twofold--;
Line 23, "EG2 core" should read --EG2core--;
Line 38, "EG2 core" should read --EG2core--;
Line 43, "EG2" should read --EG2- --; and
Line 49, "EG2 core" should read --EG2core--.

COLUMN 13:

Line 38, "Purity" should read (add) --A small amount of a higher pI protein (CBH2, pI=6.0) elutes just prior to EG2. Purity--; and
Line 39, "PAGE Beclman" should read --PAGE Beckman--.

COLUMN 14:

Line 10, "EGV core" should read --EGVcore--;
Line 11, "EGV core" should read --EGVcore--; and
Line 59, "After a" should read --After--.

COLUMN 15:

Line 23, "EG2 core" should read --EG2core--;
Line 27, "wishing to be bound by" should read --restriction to--;
Line 28, "amount on" should read --amount of--; and
Line 40, "EG2 Core" should read --EG2core--.

COLUMN 16:

Line 3, "Voltage" should read --voltage--;
Line 15, "peals" should read --peaks--;
Line 26, "of" should be deleted;
Line 54, "EG1 core" should read --EG1core-- and "EG2 core" should read --EG2core--;

CERTIFICATE OF CORRECTION (continued)
U.S. Pat. No. 8,012,721 B2 and
Line 65, "Gile's et al.," should read --Gilkes et al.,--.

COLUMN 17:

Line 1, "Optization" should read --Optimization--;
Line 13, "Nidetzlcy et al.," should read --Nidetsky et al.,--;
Line 26, "as follow:" should read --as follows:--;
Line 27, "lingocel-" should read --lignocel- --;
Line 38, "lingocellulosic" should read --lignocellulosic--;
Line 41, "total" should read --the total--; and
Line 44, "enzyme" should be deleted.

COLUMN 18:

Line 10, "enzymes," should read --enzymes--; and
Line 14, "CBH" should read --CBH enzymes--.